United States Patent [19]
Mueller

[11] Patent Number: 5,359,416
[45] Date of Patent: Oct. 25, 1994

[54] SYSTEM AND PROCESS FOR DETECTING AND MONITORING SURFACE DEFECTS

[75] Inventor: Mark K. Mueller, West Point, Utah

[73] Assignee: Thiokol Corporation, Ogden, Utah

[21] Appl. No.: 963,572

[22] Filed: Oct. 19, 1992

[51] Int. Cl.$^5$ ............................................. G01N 21/47
[52] U.S. Cl. ..................................... 356/371; 356/446
[58] Field of Search ..................... 356/371, 237, 446; 250/562, 572

[56] References Cited

U.S. PATENT DOCUMENTS

| | | | |
|---|---|---|---|
| 4,417,149 | 11/1983 | Takeuchi et al. | 250/563 |
| 4,449,818 | 5/1984 | Yamaguchi et al. | 356/237 |
| 4,538,909 | 9/1985 | Bible et al. | 356/237 |
| 4,598,997 | 7/1986 | Steigmeier et al. | 356/237 |
| 4,614,427 | 9/1986 | Koizumi et al. | 356/237 |
| 4,629,319 | 12/1986 | Clarke et al. | 356/237 |
| 4,681,442 | 7/1987 | Wagner | 356/237 |
| 4,688,939 | 8/1987 | Ray | 356/237 |
| 4,692,943 | 9/1987 | Pietzsch et al. | 382/8 |
| 4,693,608 | 9/1987 | Kitagawa et al. | 356/394 |
| 4,741,621 | 5/1988 | Taft et al. | 356/376 |
| 4,759,072 | 7/1988 | Yamane et al. | 382/8 |
| 4,875,170 | 10/1989 | Sakurai et al. | 364/507 |
| 4,920,385 | 4/1990 | Clarke et al. | 356/237 |
| 5,030,008 | 7/1991 | Scott et al. | 356/376 |
| 5,048,967 | 9/1991 | Suzuki et al. | 356/401 |
| 5,108,176 | 4/1992 | Malin et al. | 356/237 |

OTHER PUBLICATIONS

Benjamin M. Dawson, Processing extends scientific vision, Laser Focus World 121-30 (Feb. 1991).
Stuart Flom, Designing Fiber Optic Lighting for Machine Vision, Vision '90 Conference Proceedings of the Machine Vision Association of the Society of Manufacturing Engineers 1-15 to 1-26 (Nov. 1990).
John D. Jenness et al., A Region Based Image Enhancement Technique for Environments with Severe Lighting Conditions, Vision '90 Conference Proceedings of the Machine Vision Association of the Society of Manufacturing Engineers 2-53 to 2-68 (Nov. 1990).
Paul P. Lin et al., Edge Detection with Subpixel Resolution and its Application to Radius Measurement via Fringe Projection Technique, Vision '90 Conference Proceedings of the Machine Vision Association of the Society of Manufacturing Engineers 4-13 to 4-28 (Nov. 1990).
Larry Schmitt, The Practical Application of Grayscale Morphology to the Inspection of Surfaces, Vision '90 Conference Proceedings of the Machine Vision Association of the Society of Manufacturing Engineers 8-31 to 8-46 (Nov. 1990).
Robert G. Kispert et al., Automatic Inspection of Surface Critical Steel, Vision '90 Conference Proceedings of the Machine Vision Association of the Society of Manufacturing Engineers 10-1 to 10-10 (Nov. 1990).
Backlighting Data Sheet, Lumitex Product Brochure (no date).

*Primary Examiner*—Richard A. Rosenberger
*Attorney, Agent, or Firm*—Madson & Metcalf; Ronald L. Lyons

[57] ABSTRACT

A system and process for detecting and monitoring defects in large surfaces such as the field joints of the container segments of a space shuttle booster motor. Beams of semi-collimated light from three non-parallel fiber optic light panels are directed at a region of the surface at non-normal angles of expected incidence. A video camera gathers some portion of the light that is reflected at an angle other than the angle of expected reflectance, and generates signals which are analyzed to discern defects in the surface. The analysis may be performed by visual inspection of an image on a video monitor, or by inspection of filtered or otherwise processed images. In one alternative embodiment, successive predetermined regions of the surface are aligned with the light source before illumination, thereby permitting efficient detection of defects in a large surface. Such alignment is performed by using a line scan gauge to sense the light which passes through an aperture in the surface. In another embodiment a digital map of the surface is created, thereby permitting the maintenance of records detailing changes in the location or size of defects as the container segment is refurbished and re-used. The defect detection apparatus may also be advantageously mounted on a fixture which engages the edge of a container segment.

28 Claims, 8 Drawing Sheets

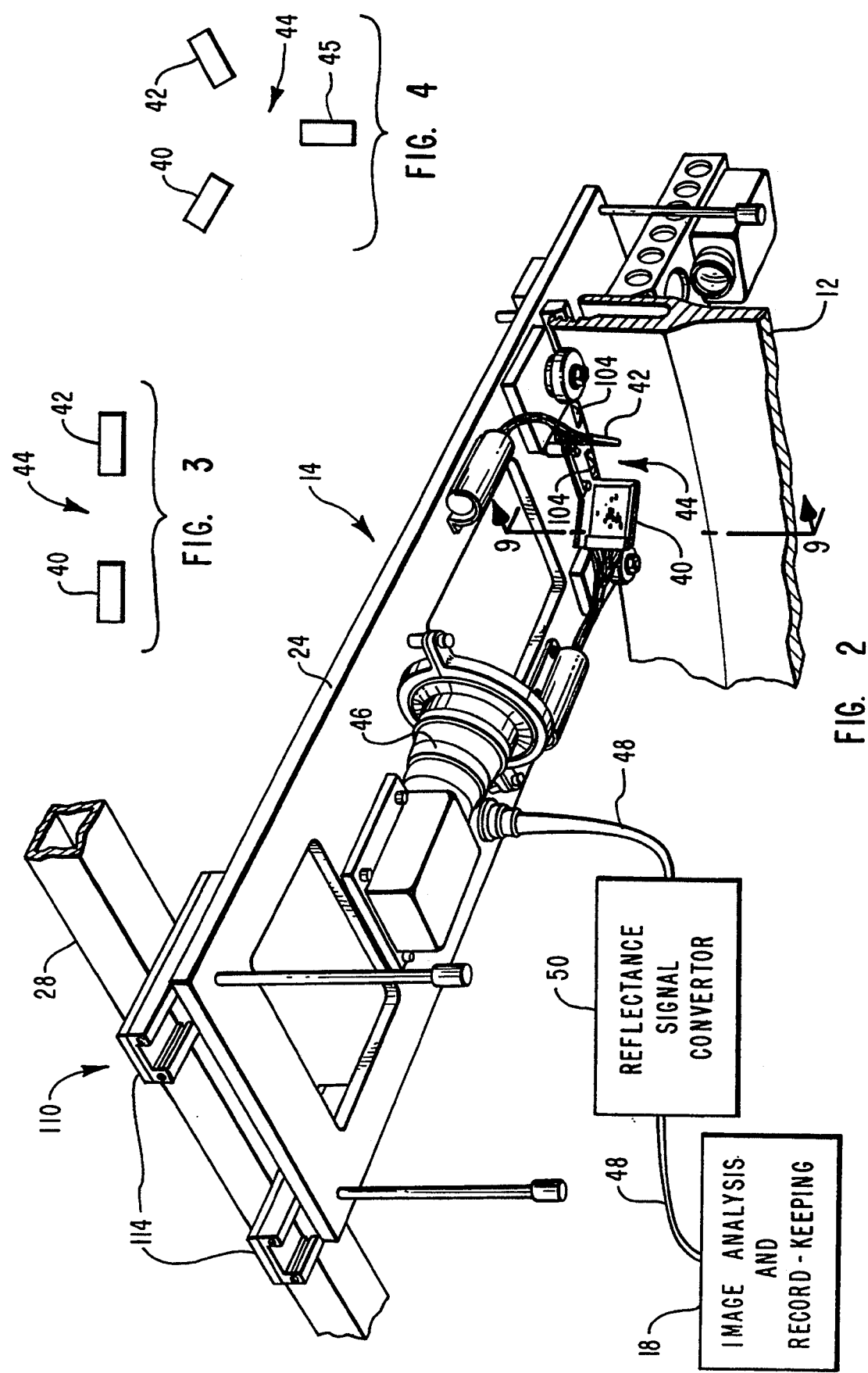

SYSTEM AND PROCESS FOR DETECTING AND MONITORING SURFACE DEFECTS

ORIGIN OF THE INVENTION

The invention described herein was made in the performance of work under NASA contract NAS8-3049-Schedule D, and is subject to the provisions of Section 305 of the National Aeronautics and Space Act of 1958, as amended (42 U.S.C. 2457).

BACKGROUND

1. The Field of the Invention

The present invention relates to a system and process for detecting and monitoring surface defects. More particularly, the present invention relates to a process for efficiently detecting and monitoring surface defects on large machined or polished metal surfaces in space shuttle booster motors by analyzing the reflection of multiple light sources directed at regions of the surface.

2. Technical Background

The United States has a long and proud history in the field of space exploration, of which the space shuttle program is an integral part. Space shuttles are lifted into space by reusable rocket booster motors. The outer case of these booster motors is constructed as a stack of interlocked segments, thereby forming a cylindrical container for solid fuel propellant. The case of a typical booster motor used on the space shuttle may include ten or more cylindrical segments in end-to-end relation. After their initial use, the empty booster motors are collected, refurbished, and re-used a dozen or more times.

During flight, these booster motors are subjected to extremely high pressures and temperatures. Because the case of the booster motor is constructed by attaching together several segments, the attachment mechanism must be able to withstand the forces imposed on the case by these extreme temperatures and pressures. Metal-to-metal contact in the attachment areas around the perimeter of the ends of the segments is one important part of the "field joint" which joins each segment with its neighboring segments.

Defects in field joint surfaces may result from a variety of causes, including in-flight stresses, machining and polishing performed during manufacturing and refurbishment, and inherent defects in construction materials. Defects in field joint surface areas are undesirable because they may hamper the desired metal-to-metal contact, and because they may provide initial focal points from which damage due to high pressure or temperature may spread.

Thus, the surfaces of field joints are carefully inspected for defects both during their original manufacture and during each refurbishment. This inspection seeks to detect defects such as bumps, depressions, gouges, burrs, scratches, "fretting", and other unexpected aberrations in the smooth metal surfaces of field joints.

The data produced during defect inspection may be compiled and stored to preserve a record of the defects. Maintaining a record of the defects on field joint surfaces serves dual goals. First, a record of surface defects permits informed decisions on whether a given segment is too defective for further use. Second, an accurate history of particular surface defects in particular segments also provides useful data in evaluating the characteristics of various materials for use in manufacturing or refurbishing container segments.

The most obvious way to inspect a surface is simply to look at it carefully. However, even though such visual inspection may permit the inspection of large areas in relatively short times, it has several drawbacks. Because human inspectors are subject to error and fatigue, inspections vary in thoroughness, accuracy, and speed. Furthermore, visual inspections alone cannot properly track the history of particular defects. Many visual inspections fail to maintain any accurate record of the defects detected. But even if a photograph or sketch is made during the inspection, such records fail to accurately quantify the precise location and extent of defects.

Optical inspection systems based on microscopes, lasers, and other technological aids provide an advancement over simple visual inspection by facilitating the collection and analysis of reflected light. However, most of these previously known approaches to optical inspection are optimized to inspect relatively small surface areas such as semiconductor chip wafers. Such wafers are at least an order of magnitude smaller than container segment field joints, so the use of such previously disclosed systems in connection with field joints or other large surfaces requires impractical amounts of time.

Because they are optimized for small inspection regions, previously disclosed systems often employ only one or two beams of light when illuminating the surface. It is not feasible to simply add more light sources to expand such systems and thereby cover larger regions. For example, many such systems employ illuminating beams which are directed normal to the surface, with optics configured to capture the reflected light for analysis. Adding additional beams to these systems would vastly complicate the optics required to gather and focus the reflected light.

Also, many previously disclosed systems employ lasers to illuminate the surface, because increased coherence in the light directed at the surface facilitates detection of disparities in the reflected light. Adding numerous lasers to increase inspection throughput would prohibitively increase the cost of such a system, and would have significant adverse effects on system size, power and cooling requirements, and other practical factors.

Many previously disclosed inspection systems and processes also fail to maintain any history of particular defects, since the articles being inspected are typically not refurbished or re-used. Accordingly, many previously disclosed systems provide no capability for recording the precise location of each defect. Similarly, many previously disclosed systems are incapable of generating digital maps of the surface which may be compared to track changes in defect location or size.

Therefore, it would be an advancement in the art to provide a system and process which efficiently and economically detects defects in large surface areas such as the field joints of booster motor container segments by gathering and analyzing light reflected off of the surface. It would be particularly beneficial if this advancement in the art did not require the use of lasers as a light source. It would also be advantageous if this advancement did not require a complex optical apparatus to gather the reflected light.

It would be a further advancement in the art to provide a system and process which permits the monitoring of particular defects over time. For instance, it would be particularly beneficial if this advancement in the art included a determination of the surface location of each defect, thereby permitting reexamination of particular defects after the container segment has been re-used. It would also be advantageous if the advancement provided digital maps, thereby permitting computer-assisted management of the defect histories and computer-assisted comparison of records of a given defect which were recorded at different points in time.

Such a system and process is disclosed and claimed herein.

BRIEF SUMMARY AND OBJECTS OF THE INVENTION

The present invention is directed to a novel system and process for detecting and monitoring defects in large surfaces such as the field joints of booster motor container segments. As used herein, "defects" includes bumps, depressions, gouges, burrs, scratches, holes, and other unexpected aberrations in the surface of an article. Defects are unexpected in that the location and extent of any particular defect is initially unknown.

In accordance with the teachings of the present invention, fiber optic cables which have been woven into light panels are employed to direct groups of semi-collimated light onto a region of the surface to be inspected. As used herein, "semi-collimated light" means a plurality of beams of non-laser light which are substantially parallel to each other. Although the presently preferred embodiment employs fiber optic light panels as light sources, it will be appreciated that virtually any source of semi-collimated light could also be employed.

The semi-collimated light is preferably directed onto the surface region at non-normal angles of expected incidence. The actual angle of incidence of a beam of light is the angle at which the beam hits the surface. As used herein, the "angle of expected incidence" of a beam of light is the angle of incidence the beam of light would have if the surface were free of defects. Thus, in a defect-free surface the angle of actual incidence equals the angle of expected incidence. The angle of actual incidence of a beam of light which hits a defect, however, differs from the angle of expected incidence of that beam.

The present invention preferably contains three fiber optic light panels, with each panel arranged to direct light onto the surface from a different location. Defects are best illuminated by light striking their sides. For instance, light which is parallel to a long narrow defect does not illuminate that defect well. Arranging the light panels such that the beams emitted from any one panel are not substantially parallel to the beams emitted from at least one other panel therefore increases the likelihood of illuminating all defects clearly.

A video camera is positioned with respect to the surface such that it gathers some portion of the light which is reflected from the surface at an angle other than the angle of expected reflectance. As used herein, the "angle of expected reflectance" of a beam of light is the complement of the angle of expected incidence, that is, one-hundred-and-eighty degrees minus the angle of expected incidence. Thus, light which strikes a defect is reflected from the surface at an angle other than the angle of expected reflectance, and the video camera gathers some portion of the light reflected from such defects.

In the presently preferred embodiment, the invention is employed to detect defects in the machined or polished metal surfaces of booster motor container segments. However, it will be appreciated by those skilled in the art that many other articles may also be successfully inspected with the process and system herein disclosed, even though they differ from container segments in shape, size, composition, finish, or other characteristics.

The video camera generates signals based on the reflected light gathered; these signals are analyzed in either analog or digital form to discern defects in the surface. The analog video camera signals may be fed directly to a video monitor for defect analysis by visual inspection of the image on the monitor. This approach to inspection is superior to unaided visual inspection of the surface because the light sources and video camera described above enhance and clarify the image of the surface defects.

Alternatively or in addition, the signals generated by the video camera may be converted into digital form in preparation for subsequent averaging, filtering, and other processing by a digital computer. Averaging, filtering, and other processing minimizes the effects of variation in ambient lighting. A digital map of the surface region is produced, in which zeroes represent defect-free locations and ones represent defects. These digital maps may be compared with one another to discern changes in a particular defect over time.

In the presently preferred embodiment, a surface position analyzer is used to align successive predetermined regions of the surface with the defect detection light source, thereby permitting inspection of a large surface region-by-region within a reasonable period of time while maintaining a precise record of the location of all defects detected. As explained below, the surface position analyzer in the presently preferred embodiment is optimized for certain structural features of booster motor container segments, but it will be appreciated that other approaches to alignment may also lie within the scope of the detection and monitoring system and process herein disclosed.

The typical outside diameter of a container segment used in constructing a space shuttle booster motor contains one-hundred-and-eighty equally spaced joint pin holes. One hole, slightly smaller than the others, is known as the "zero degree" pin hole; the other holes are denoted the 1 degree pin hole, 2 degree pin hole, and so forth, proceeding in a predetermined direction around the perimeter from the zero degree pin hole.

The presently preferred embodiment utilizes a fiber optic light panel as an alignment light source to determine the position of the system with respect to these pin holes. (This light panel is in addition to and distinct from the light panels used to illuminate the surface.) The alignment light source is arranged such that it either shines through a pin hole or is partially obscured by the web between pin holes. This light is detected by a line scan gauge. The line scan gauge generates signals which are analyzed, thereby determining the position of the pin holes relative to the line scan gauge.

The line scan gauge is mounted on a platform. The video camera and surface-illuminating light sources are preferably also mounted on this platform, thereby ensuring that the line scan gauge and the video camera maintain fixed positions relative to each other. Therefore, by using the line scan gauge to sense the light passing through a pin hole, it is possible to determine the position of the pin hole relative to the line scan gauge, and thus to determine the position of the surface being inspected relative to the video camera.

The platform on which the video camera and line scan gauge are mounted is part of a larger mounting fixture. This mounting fixture maintains the desired relative positions of the inspected region, the surface-illuminating light sources, the video camera, the pin holes, the alignment light source, and the line scan gauge. In the presently preferred embodiment, the mounting fixture is optimized for the inspection of booster motor container segments. However, it will be apparent to those skilled in the art that other mounting fixtures, whether used in connection with container segments or with other articles, may also lie within the scope of the present invention.

The platform is preferably attached to a supporting chord beam which stretches from one point on the edge of the container segment to another point on that edge. The mounting fixture is mounted on a container segment such that the two ends of the chord beam and the platform are releasably and slidably supported by the edge of the container segment. Thus, the fixture, together with attached light sources, video camera, and line scan gauge may be rotated around the container segment as the field joint surface is inspected region-by-region.

Thus, it is an object of the present invention to provide a system and process for efficiently and effectively detecting and monitoring defects in large surfaces.

It is a further object of the present invention to detect surface defects without the use of lasers, complex optical systems, or carefully controlled ambient lighting.

It is also an object of the present invention to permit monitoring of numerous individual surface defects over the life of an article by creating and maintaining records of the changes in defect location and size after the article is re-used or refurbished.

It is an additional object of the present invention to facilitate detecting and monitoring defects in large surfaces by quantifying and automating inspection and monitoring processes previously performed informally or not at all.

These and other objects and advantages of the present invention will become more fully apparent by examination of the following description of the preferred embodiments and the accompanying drawings.

BRIEF DESCRIPTION OF THE DRAWINGS

In order that the manner in which the above-recited and other advantages and objects of the invention are obtained, a more particular description of the invention briefly described above will be rendered by reference to the appended drawings. Understanding that these drawings only provide data concerning typical embodiments of the invention and are not therefore to be considered limiting of its scope, the invention will be described and explained with additional specificity and detail through the use of the accompanying drawings in which:

FIG. 2 is a perspective view of one embodiment of the image acquisition apparatus illustrating the light sources and light detector in their working relation to the surface being inspected and to each other.

FIG. 3 is a plan view of the light sources of FIG. 2 as seen from the video camera.

FIG. 4 is a plan view of the light sources as seen from the video camera of an alternative light source configuration.

DETAILED DESCRIPTION OF THE PREFERRED EMBODIMENTS

Figure 1:
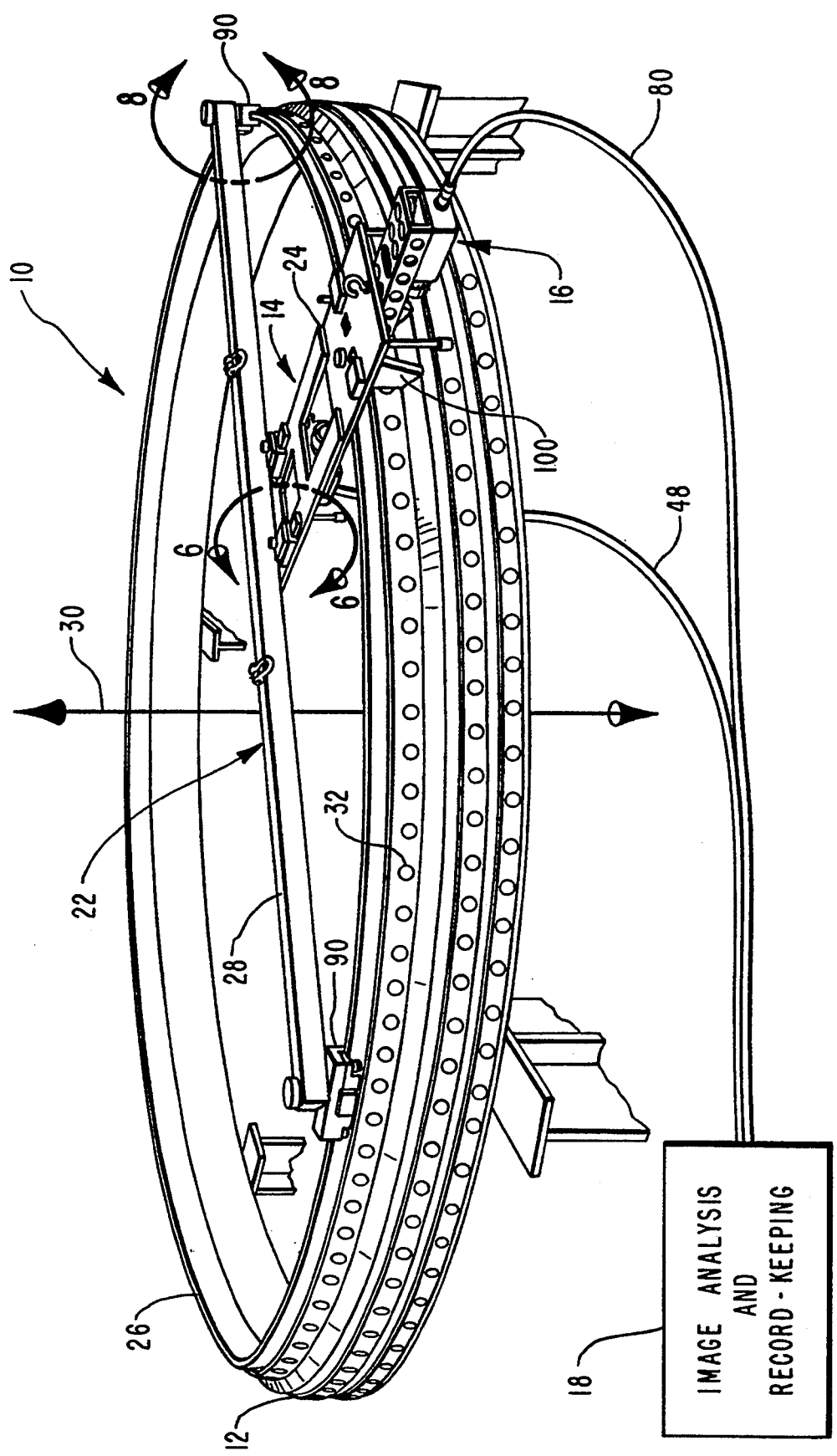
FIG. 1 is a perspective view of one embodiment of the present invention as it appears when mounted on a booster motor container segment.

Reference is now made to the figures wherein like parts are referred to by like numerals throughout. With particular reference to FIG. 1, a system for detecting defects in a surface in accordance with the present invention is generally designated at 10. The system of the present invention may be used to detect, evaluate, record, and trace the history of a wide variety of defects in large surfaces.

For example, in the production and refurbishment of reusable solid rocket motors wherein data concerning defects in container segment field joints is needed, typical defects may include bumps, depressions, burrs, or other aberrations in the smooth metal surface of a field joint. Defects occur in various shapes and sizes, but those of concern typically measure at least 0.002 inches in either width or length. The present invention is well-suited to detect and monitor such defects on the field joints of container segments which are used in constructing space shuttle booster motors.

The embodiment illustrated in FIG. 1 shows the system 10 mounted on a container segment 12 from a booster motor designed for use on the space shuttle. Field joint surface areas vary in size, but are typically about 0.6 inches high by 450 inches long (the latter dimension being the approximate circumference of the container segment). Although the embodiment illustrated in FIG. 1 is configured for use on a substantially cylindrical member, one of skill in the art will appreciate that different embodiments of the invention may be successfully configured for use on a variety of shapes of articles.

The system 10 includes an image acquisition apparatus 14, a positioning indicia locator 16, an image analysis and record-keeping apparatus 18, and a mounting fixture 22. The mounting fixture 22 maintains the desired positional relationships between the container segment 12, the image acquisition apparatus 14, and the positioning indicia locator 16. Images of the surface of the container segment 12 are obtained using the image acquisition apparatus 14. Image information from the image acquisition apparatus 14 and positional information from the positioning indicia locator 16 is transmitted over cable 48 and cable 80, respectively, to the image analysis and record-keeping apparatus 18. Processing, analysis, storage, and retrieval of the image and positional information permit the system to detect and monitor surface defects.

The mounting fixture 22 includes a platform 24 and a chord beam 28. The platform 24 is supported at one end by the chord beam 28. The opposite end of the platform 24 and both ends of the chord beam 28 are supported by an edge 26 of the container segment 12.

The image acquisition apparatus 14 and the positioning indicia locator 16 are each attached to the platform 24, thereby fixing them in a predetermined positional relationship with respect to each other and with respect to the container segment 12. As explained in greater detail below, the image analysis and record-keeping apparatus 18 utilizes data from the positioning indicia locator 16 to determine the precise location on the container segment 12 of defects detected in images acquired by the image acquisition apparatus 14.

The embodiment of the image acquisition apparatus 14 illustrated in FIG. 2 includes two light sources, 40 and 42. As further illustrated in FIG. 5, these light sources 40 and 42 are positioned such that they direct beams of light onto a region 44 of the field joint surface of the container segment 12. In the presently preferred embodiment, the light sources 40 and 42 are fiber optic light panels produced by Lumitex, Inc. of North Royalton, Ohio, but different embodiments may employ other sources of light. In this embodiment, each light panel measures approximately 1.25 by 1.75 inches and incorporates approximately two hundred optic fibers 41 carrying light from a source 43 which is also mounted on the platform 24.

Figure 6:
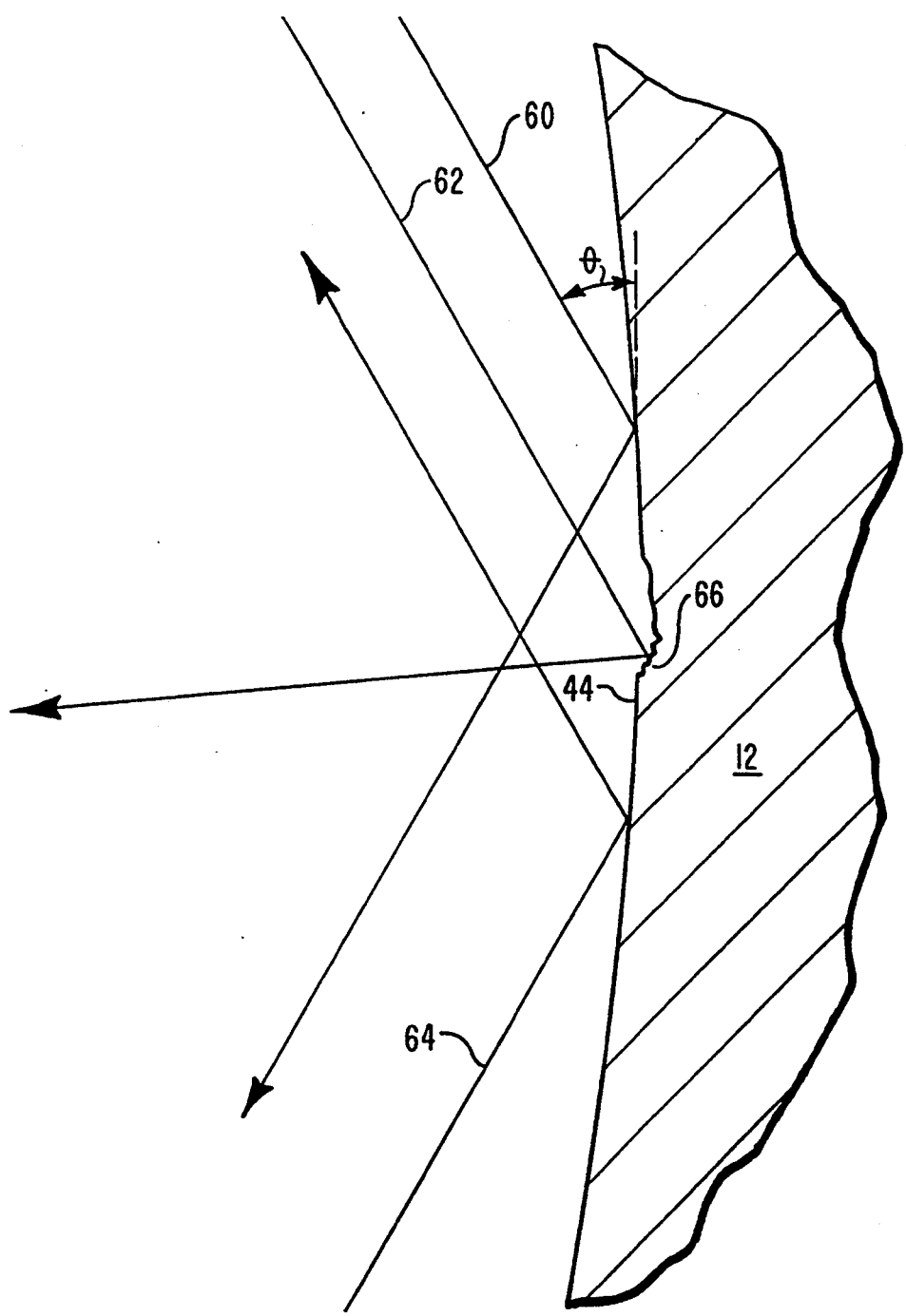
FIG. 6 is an enlargement of the surface inspection region taken along line 6—6 of FIG. 5, illustrating the paths taken by beams of light striking the surface during inspection.

Each of the fiber optic light panels 40 and 42 preferably emits semi-collimated light. That is, all the beams of light emitted from a given panel are substantially parallel; unlike laser beams, however, semi-collimated beams are not coherent. The panels 40 and 42 are preferably positioned such that the group of beams emitted from one panel is substantially nonparallel to the group of beams emitted from the other panel. For example, in the illustrated embodiment, the light sources 40 and 42 lie 180 degrees apart when viewed along a line normal to the region 44, as illustrated in FIG. 3. Similarly, FIG. 6 shows that two beams of light 60 and 62 which are emitted from the same panel are substantially parallel to each other, while neither of beams 60 and 62 is parallel to a beam of light 64 emanating from the other panel. The diagram of FIG. 4 illustrates a presently preferred configuration in which a third light source 45 has been added and the three light sources 40, 42, and 45 lie 120 degrees apart when viewed along a line normal to the region 44.

Figure 5:
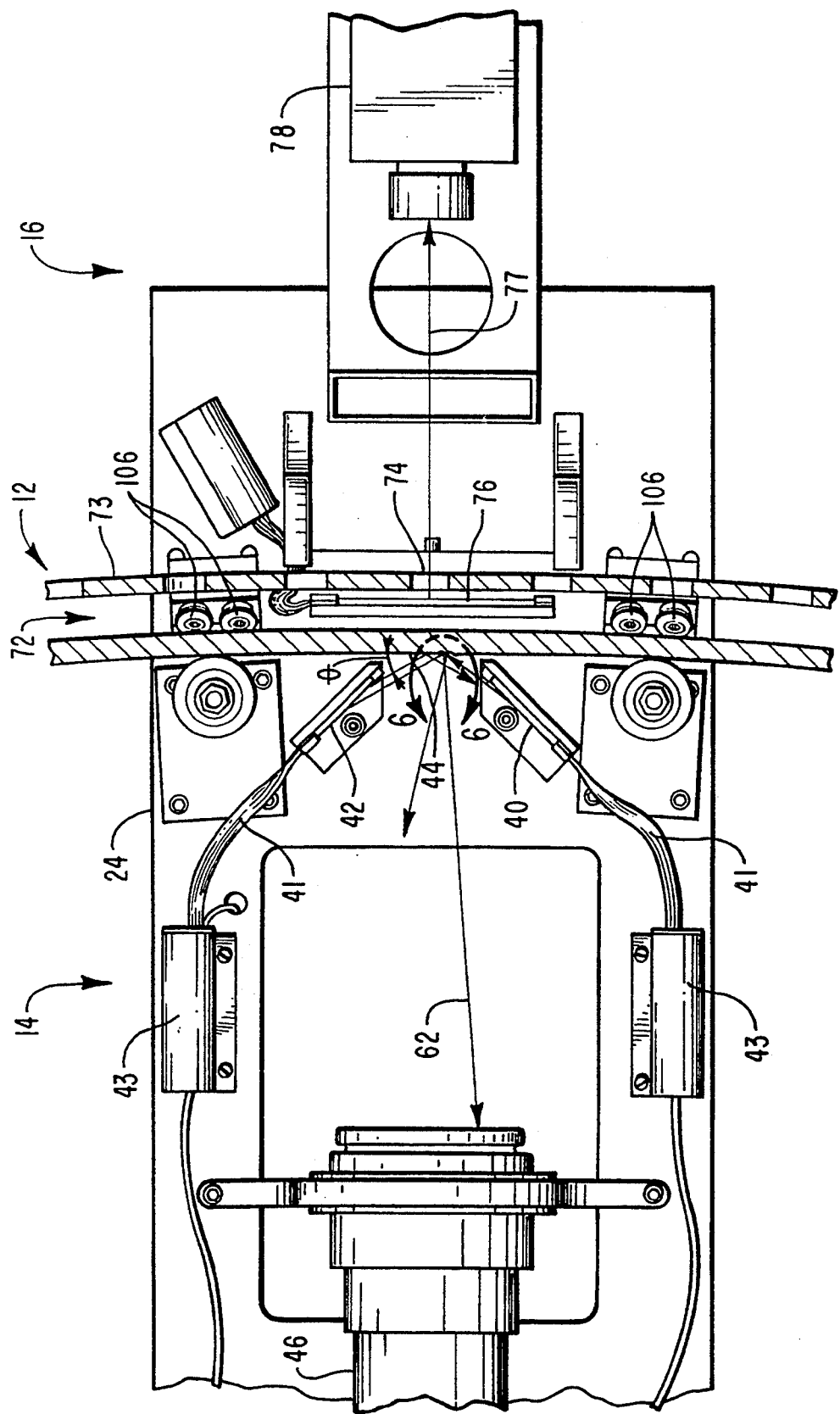
FIG. 5 is a plan view of the image acquisition apparatus of FIG. 2.

As illustrated in FIG. 5, a video camera 46 is positioned substantially normal to the region 44. By thus positioning camera 46, some of the beams of light emitted by fiber optic light panels 40 and 42 which are reflected off defects in the surface region 44 may be detected. In the embodiment illustrated in FIGS. 2 and 5, the video camera 46 is focused on a region 44 that is 0.60 inches high by 1.35 inches wide; this corresponds to a one-degree arc of the container segment 12 plus an overlap of 0.05 inches on each side of the region to compensate for human error in positioning the mounting fixture. A variety of commercially available video cameras or equivalent light detectors may be used, such as a Pulnix model TM-80 video camera controlled by a Camera Control Unit model CCU-80, with a Nikkor fixed focus 60 mm lens mounted on the camera via a Nikkor-to-C adaptor, available from GWH and Associates of Boulder, Colo.

As illustrated in FIGS. 5 and 6, the panels 40 and 42 are preferably positioned such that the beams of light they emit are directed to strike the region 44 of the surface at a non-normal angle of expected incidence. In the presently preferred embodiment, the light sources 40 and 42 are positioned such that the angle of expected incidence $\theta$ is approximately 50 degrees. Of course, one of skill in the art will appreciate that the present invention could also be configured with a light source positioned normal to region 44 and with video camera 46 positioned at some non-normal angle with respect to region 44 to collect beams of light reflecting off defects on the surface.

When an appropriate angle of expected incidence $\theta$ is employed, beams of light striking the surface region 44 at points free of defects are reflected away from video camera 46, as shown in FIG. 5. Thus, the two beams 60 and 64 shown in FIG. 6 strike defect-free points on the region 44 and are reflected away from the video camera. Beams of light striking defects, however, may be reflected toward the camera. For example, beam 62 is reflected from a defect 66 toward the camera. Thus, highlights in the images acquired by the image acquisition apparatus correspond to defects in the region 44.

It will be apparent from the foregoing that the appropriate angle of expected incidence $\theta$ depends on the equipment used to detect light reflected from the surface and on the shape and size of the defects. As FIGS. 5 and 6 suggest, an appropriate value for $\theta$ may be determined by focusing the video camera 46 on a test region 44 which contains a typical defect 66 and varying the angle of expected incidence $\theta$ until the contrast is maximized in the resulting image.

As illustrated in FIG. 2, the video camera 46 generates signals corresponding to the reflected light it detects, and transmits these signals along cable 48 to a reflectance signal convertor 50. The reflectance signal convertor 50 converts the signals generated by the video camera 46 into analyzable reflectance signals.

In some embodiments of the present invention, the reflectance signal convertor 50 may convert the analog signals from video camera 46 into digital signals which are transmitted through cable 48 to a computer in the image analysis and record-keeping apparatus 18 for further processing and analysis. In a presently preferred embodiment of the invention, 16 images of each region 44 are captured by the video camera 46 and averaged to form one representative image of the region 44.

Analog-to-digital conversion of the signals from video camera 46 may be performed by commercially available video image acquisition hardware such as a Targa 32 image capture board in an IBM compatible personal computer. Computer processing within the image analysis and record-keeping component 18 may be performed by commercially available computers, such as an IBM compatible 80386-based personal computer with no floating point processor communicating through a 3C505 Ethernet board and AUI adaptor with a Silicon Graphics Iris-4D workstation. In a presently preferred embodiment of the invention, a commercially available 1 megabyte Intel Above Board and an Arcnet board are also employed.

In other embodiments, the reflectance signal convertor 50 may pass the signals from the video camera 46 to a commercially available video monitor (not shown) for visual inspection. In such an embodiment, the image analysis and record-keeping component 18 would include the video monitor as well as a human inspector who visually examines the images. As explained in detail below, such alternative embodiments may also employ computer processing to improve the quality of an image before it is displayed on a monitor.

Figure 7:
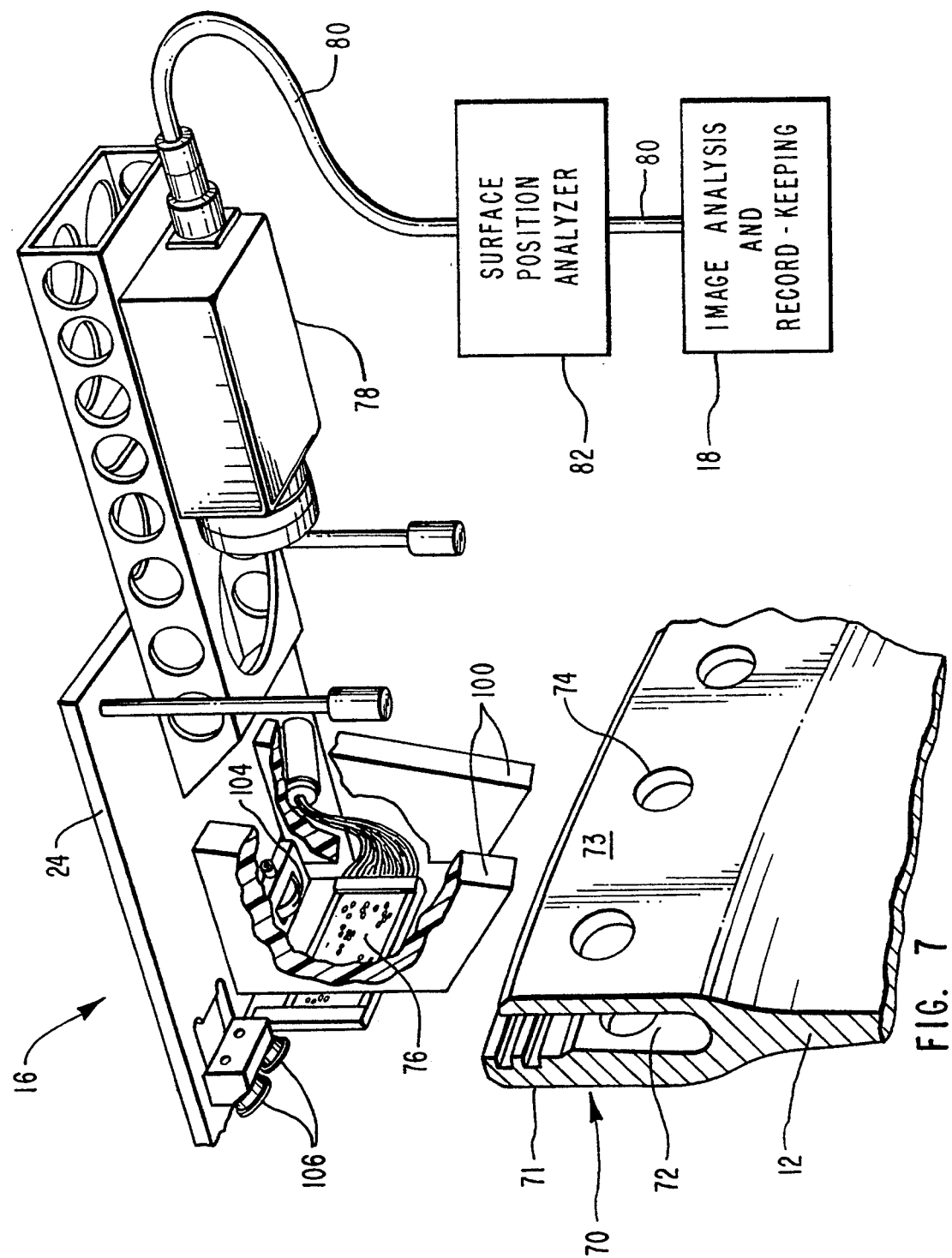
FIG. 7 is a perspective view of one embodiment of a positioning indicia locator built in accordance with the teachings of the present invention.

The positioning indicia locator 16 illustrated in FIG. 7 provides information whereby the system can precisely determine the location of defects detected on the surface of the container segment 12. The positioning indicia locator 16 includes a light sensor 78 which transmits a signal through a cable 80 to a surface position analyzer 82. In a presently preferred embodiment, the light sensor 78 is a commercially available line scan gauge, such as the MicroSwitch model HVS-256-133-CS2, available from Motion Solutions of Englewood, Colo.

The position indicia locator 16 further includes a positioning indicia light source 76 positioned on platform 24 collinearly with light sensor 78. Thus, when the container segment 12 is positioned such that a pin hole 74 is located between light source 76 and light sensor 78, as illustrated in FIGS. 5 and 7, light sensor 78 detects this condition by sensing light emitted by light source 76. Light sensor 78 then generates a corresponding signal which is transmitted through cable 80.

The analyzer 82 shown in FIG. 7 uses the signal from light sensor 78 to determine the position of the mounting fixture 22 as it rotates about the central axis of the container segment 12. The analyzer 82 transmits this positional information to the image analysis and record-keeping apparatus 18, thereby permitting the system to link together successive images as each region is inspected to form a map of the entire inspected surface of the container segment 12.

As illustrated in FIG. 7, the upper portion of the container segment 12 forms a Y-shaped tang 70, which defines a tang channel 72. The surface of the container segment 12 being inspected lies on the inner branch 71 of the tang 70. The outer branch 73 of the tang 70 is pierced by 180 regularly spaced pin holes, such as pin hole 74. The centers of these pin holes are spaced at 2.5 inch intervals. Each pin hole has a diameter of 0.99 inches, except the zero degree pin hole 32, which is slightly smaller to distinguish it from the other pin holes and thereby identify it as the zero degree pin hole 32.

The positioning indicia light source 76 is positioned within the tang channel 72. In the presently preferred embodiment, this light source 76 is a fiber optic light panel of the same general type as the light sources 40 and 42 used in the image acquisition apparatus 14. All three panels 40, 42 and 76 are wired in series to a power supply, such as an Acopian model A018NX100 power supply providing 1 amp at 15 volts, available from Acopian of Easton, Pa.

The positioning indicia light source 76 is preferably dimensioned and positioned such that as the mounting fixture is rotated about the container segment 12, light from the light source 76 is continuously visible to the light sensor 78 through at least a portion of at least one pin hole. As illustrated in FIG. 5, for example, light 77 from the light source 76 is directed through pin hole 74 and into light sensor 78. Further rotation of the system about the container segment 12 will permit some light to pass through the adjacent pin hole before the original pin hole 74 is moved completely past the light source 76. In a presently preferred embodiment, the light panel 76 is approximately 1-inch high and at least 1.5 inches wide, because pin holes are 0.99 inches in diameter with centers 2.5 inches apart.

As the container segment 12 and the light sensor 78 are moved relative to each other, the pin hole 74, illuminated by light 77 from the light source 76, moves across the field of view of the line scan gauge 78. In the presently preferred embodiment, the line scan gauge 78 is focused on a region of the outer tang branch 73 which is approximately 1.6 inches wide, so at least one pin hole is always in the field of view of the gauge 78.

The line scan gauge 78 produces signals which vary according to the relative position of the illuminated pin hole. As illustrated in FIG. 7, these signals are transmitted by cable 80 to surface position analyzer 82. Because the surface region being inspected does not move relative to the pin hole 74, and the line scan gauge 78 does not move relative to the image acquisition apparatus 14, these signals from the line scan gauge 78 also vary according to the position of the region 44 with respect to the image acquisition apparatus 14. Thus, signals from the positioning indicia locator 16 permit the image analysis and record-keeping apparatus 18 to determine the position on the container segment 12 of any detected defects.

The specific configuration of the positioning indicia locator 16 illustrated in FIGS. 5 and 7 is optimized to conform with certain structural features of the container segment 12. It will be readily apparent to those skilled in the art, however, that other positioning indicia locators within the scope of the claimed invention may also be used to detect and monitor surface defects in articles other than booster motor container segments.

Figure 8:
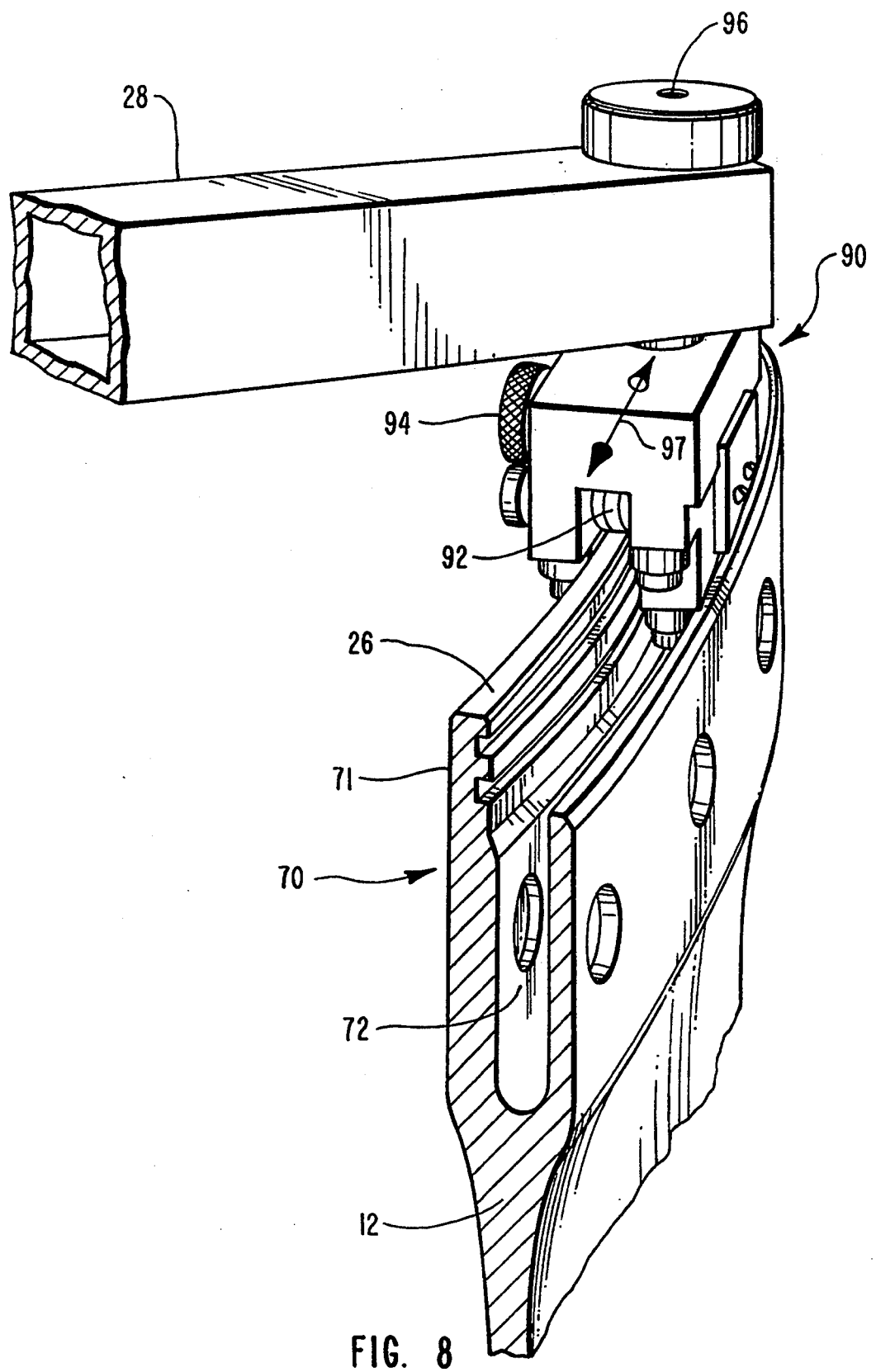
FIG. 8 is a perspective view taken along line 8—8 of FIG. 1, illustrating one end of the mounting fixture chord beam as it engages an edge of the container segment.

The defect detection system of the present invention is advantageously configured to mount upon a container segment and be easily moved about the perimeter of the container segment to thereby facilitate detection of defects along the field joint areas. As illustrated in FIG. 1, each end of chord beam 28 rests upon a clevis foot 90. And, as shown in FIG. 8, each clevis foot 90 straddles the inner branch 71 of the tang 70.

Each clevis foot 90 is configured with rollers 92 that rest on the edge 26 of the container segment 12, thereby facilitating smooth rotation of the mounting fixture about the central axis of segment 12. A locking knob 94 is provided on each clevis foot 90. By tightening locking knob 94, the corresponding clevis foot 90 is locked, thereby preventing undesired movement of the mounting fixture and facilitating inspection of a segment having a central axis which is not perfectly vertical.

To accommodate movement of the mounting fixture 22 around a container segment which is not perfectly circular, the clevis foot 90 is rotatably attached to the end of the chord beam 28 by a pin 96. As illustrated in FIG. 8, the rolling axis 97 of the clevis foot 90 is essentially tangential to the container segment 12. The angle between the chord beam 28 and rolling axis 97, as viewed from above the container segment 12, therefore varies with the curvature of the container segment 12. Thus, permitting the clevis foot 90 to rotate relative to the chord beam 28 allows the mounting fixture 22 to compensate for variations in the curvature of the container segment 12. Attaching the clevis foot 90 to the chord beam 28 by the pin 96 permits the clevis foot 90 to so rotate.

Figure 9:
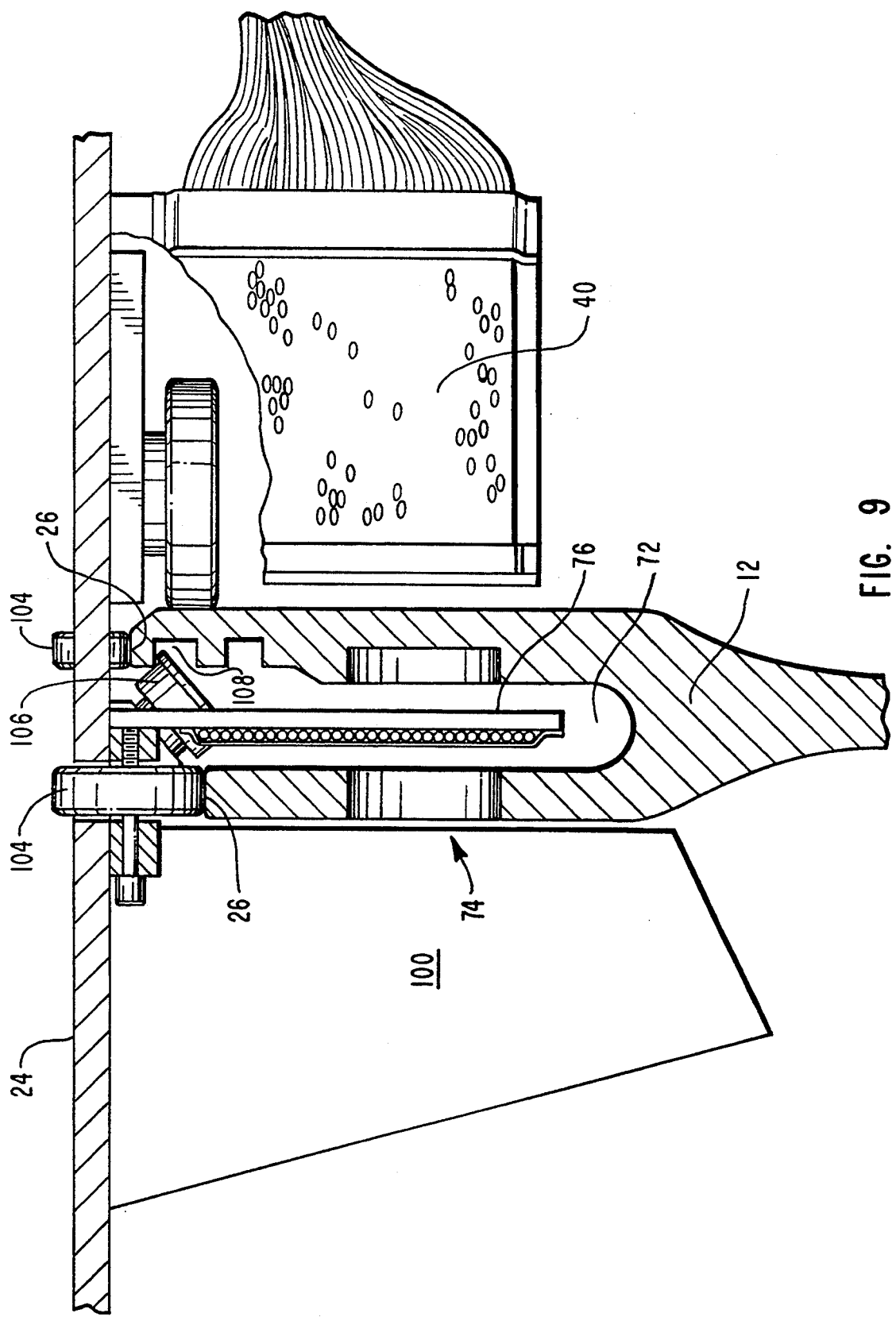
FIG. 9 is a cross-sectional view taken along line 9—9 of FIG. 2, illustrating the mounting fixture platform as it engages an edge of the container segment.

As shown in FIG. 1, the platform 24 of the mounting fixture 22 also rests on the edge 26 of the container segment 12. As illustrated in FIG. 9, the platform 24 is supported by rollers 104 which rest on the edge 26 of the container segment 12. Furthermore, the platform 24 engages the edge 26 of the container segment 12 through several locking feet 106, as shown in FIG. 5, 7, and 9. As illustrated in FIG. 9, these locking feet 106 releasably engage a smaller channel 108 within the tang channel 72, thereby stabilizing the position of the mounting fixture 22 relative to the container segment 12. The locking feet 106 are preferably urged into the smaller channel 108 by springs (not shown).

When the mounting fixture 22 illustrated in FIG. 1 rotates about a container segment which is not perfectly circular, the radial distance between the chord beam 28 and the edge 26 of the container segment 12 varies. As illustrated in FIG. 9, the platform locking feet 106 travel within the tang channel 72 at the edge 26 of the container segment 12. To compensate for the variance in the radial distance between the chord beam 28 and the edge 26 of the container segment 12, the mounting fixture is preferably configured with a slide 110, as shown in FIGS. 2 and 10, which permits radial movement of the platform 24 perpendicular to the central vertical axis of the container segment, thereby allowing rotation of the mounting fixture even when the container segment is not perfectly circular.

Figure 10:
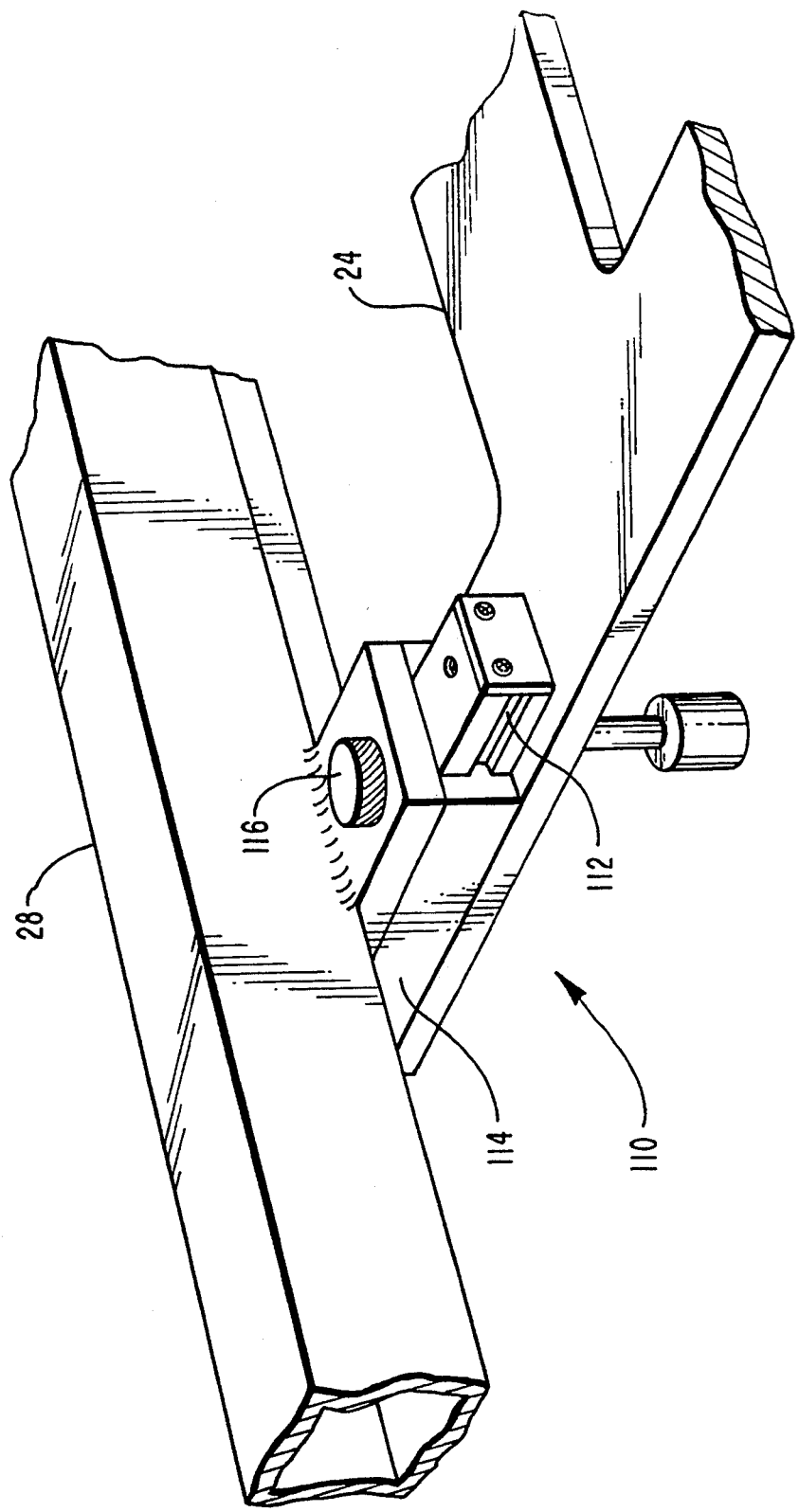
FIG. 10 is a perspective view of one embodiment of a compensation means for use with the mounting fixture, taken along line 10—10 of FIG. 1.

As illustrated in FIG. 10, a slide groove 112 mounted on the platform 24 engages a slide tongue 114 mounted on the chord beam 28. The locking knob 116 may be tightened to prevent undesired movement of the slide 110, such as when the mounting fixture is being initially mounted on the container segment.

With reference now to FIG. 1, when using the system 10 according to the teachings of the present invention, the mounting fixture 22 is first mounted on the container segment 12. Next, the mounting fixture 22 is rotated around the central vertical axis 30 of the container segment 12 until the zero degree pin hole 32 is centered in the field of view of the line scan gauge 78 or other light sensor used by the positioning indicia locator 16. In the presently preferred embodiment, the mounting fixture 22 is rotated by hand, although motorized rotation could be incorporated in other embodiments.

After this initial positioning, inspection of the field joint surface of the container segment 12 may commence. Inspection may proceed region-by-region until the entire field joint surface has been examined. The system of the present invention may also be used to inspect particular predetermined regions which are not necessarily contiguous. Additionally, the system may be used independently of the positioning indicia locator 16 to scan for or examine defects without recording or utilizing their precise location on the container segment 12.

Initially, one region is inspected by directing light onto the region 44 from the light sources 40 and 42, as illustrated in FIGS. 2 and 5. Some of the light reflected by surface defects is detected by video camera 46. That signal is then utilized to generate reflectance information by digitizing, averaging, filtering or otherwise processing or transmitting the video image. The reflectance information is then analyzed, such as by comparing two maps of the same defect or by visually inspecting a processed image of the region 44. The image information may also be correlated with positional information from the positioning indicia locator to determine the precise location of defects on the surface of the container segment 12. Records of the image and positional information may also be created or modified.

To reposition the system after a given region is inspected, the mounting fixture 22 illustrated in FIG. 1 may be incrementally rotated one degree around the central vertical axis 30, thereby bringing the next region into the field of view of the image acquisition apparatus 14. If the edge 26 of the container segment 12 is not level, the locking knobs 94 shown in FIG. 8 may be tightened to prevent the mounting fixture from slipping out of the desired position.

Since a booster motor container segment contains 180 equally spaced pin holes around its perimeter, each one-degree rotation of the system about the segment alternately places a pin hole or a portion of the web between two pin holes in the center of the field of view of the line scan gauge 78. For example, as viewed in FIG. 5, pin hole 74 is centered in the field of view of the line scan gauge 78. When the web between pin holes is centered, light from the fiber optic light panel 76 shows only at the extreme edges of the field of view of the line scan gauge 78.

As illustrated in FIG. 1, the positioning indicia locator 16 and the image acquisition apparatus 14 rotate in lock-step together around the central vertical axis 30 of the container segment 12 because they are both mounted on the same platform 24. Thus, repositioning the positioning indicia locator 16 also repositions the image acquisition apparatus 14. Software counters of a type familiar to those of skill in the art may be used by the image analysis and record-keeping component 18 to keep track of how many pin holes have passed the line scan gauge 78, thereby making it possible to determine the absolute circumferential position of the mounting fixture 22 and hence the position of the region being inspected.

Furthermore, it is also possible through straightforward calculations to determine the precise location within a region of any defect shown in an image of the region, because the positional relationship between points in the image and points within the region is known. In the presently preferred embodiment, for instance, each element of an image, i.e., each "pixel", corresponds to a portion approximately 0.0026 inches wide by 0.0023 inches high of the region being inspected; each image is 512 pixels wide by 256 pixels high.

After the mounting fixture is repositioned, beams of light are directed at the region which is being inspected. The light sources 40 and 42 shown in FIGS. 2 and 5 are constantly illuminated while the image acquisition apparatus 14 is in use. When the region 44 is free of defects, beams of light striking the surface are reflected away from the video camera 46, as occurs with beams 60 and 64 in FIG. 6. Beams of light striking defects, however, may be reflected toward the camera 46. For example, beam 62 is reflected from a defect 66 toward the camera 46.

In general, more light is reflected into the camera 46 from defects than is reflected into the camera from the smooth surface surrounding the defects. In this way, defects show up as highlights in the images acquired by the image acquisition apparatus 14.

Directing beams at the region to be inspected in substantially non-parallel groups decreases the risk that some defect will not be highlighted. The defect 66, for instance, is not highlighted by beam 64 or by other beams from the same panel as that beam 64 because the position of the sides of the defect 66 relative to that panel causes beams from that panel to reflect away from the camera. But the defect 66 is highlighted by beams directed from another panel, such as beam 62, because those beams are not substantially parallel to the beams from the first panel and hence do not reflect in the same direction.

Another embodiment, illustrated in FIG. 4, employs three light panels rather than two, with the three panels positioned such that the beams of light from each panel are substantially non-parallel to the beams from the other two panels, thereby decreasing even further the risk that a defect will escape detection. Four or more light panels could, of course be employed to direct light from even more positions, but semicollimated light such as that from fiber optic light panels includes a diffuse component which undesirably reduces image contrast if too many panels are used. Hence, three panels appear to be the optimal trade-off between too much diffuse light on the one hand, and beams directed from too few positions on the other.

Referring again to FIG. 2, 16 images of each region 44 are preferably gathered by the video camera 46 and converted into digital form by the reflectance signal convertor 50. In each image, a process familiar to those skilled in the art is used to assign each pixel an initial digital value ranging from 0 to 255, which represents a grey scale ranging from black to white, respectively.

The 16 images are preferably arithmetically averaged to obtain one image of the region 44 which is utilized by the image analysis and record-keeping component 18. That is, the 16 pixels located at a given position in the image are added together, and the result is divided by 16. This process is performed for each pixel in the 512 by 256 pixel image. Sixteen images are preferably averaged because it provides satisfactory experimental results and, being a power of two, permits rapid division operations in digital computers. As averaging minimizes the effects of transient differences in ambient lighting, the present invention is well-suited for use in normally illuminated workplaces which contain light sources in addition to the fiber optic light panels 40 and 42.

It will also be appreciated by one skilled in the art that the computers within the image analysis and record-keeping component 18 may be advantageously employed to filter noise from digital images of the region 44. In the presently preferred embodiment, image pixels are processed through a high-pass filter in the form of a Fourier transform in the circumferential direction of the container segment 12. The amplitude of the frequency components from DC to a frequency equivalent to 0.5 cycles per the length of the image are set to zero, and then the inverse transform is performed.

The arithmetic values produced by the high-pass filter are then "clamped". Clamping sets to zero every pixel which is less than a certain threshold, and sets every other pixel to one, thereby changing an image which contains black, white, and various shades of grey into an image containing only black and white. An appropriate clamping threshold level may be determined by focusing the video camera on a test region which contains a minimal defect and gradually decreasing the threshold value from 255 until the defect becomes visible in the clamped image of the region. The threshold value may also be made to depend upon the particular image being clamped. Thus, in the presently preferred embodiment, the threshold value is determined by adding together all the pixel values of the image after digitization but before applying the noise filter, dividing by the number of pixels (512 times 256), and dividing once again by four.

Digitizing, filtering, and clamping the video camera signal therefore produces a map of the inspected region in which defects correspond to ones and smooth surface corresponds to zeros. It will be apparent to one skilled in the art that these maps may be stored, retrieved, and compared with one another to determine changes in defects over the life of the container segment or of any other article subject to inspection for surface defects.

From the foregoing it will be appreciated that the present invention provides a system for detecting and monitoring bumps, scratches, and other aberrations in a regular reflective surface such as the smooth metal surface of a container segment field joint. The present invention permits the reasonably rapid detection of such defects in surfaces much larger than those contemplated by many earlier systems, and does so without the use of expensive lasers or complex optics. Additionally, the present invention pinpoints precisely the location of each defect, and maintains records which permit one to monitor the changes in a particular defect after the article inspected is re-used or refurbished. Importantly, the present invention provides an efficient and effective system and process for inspecting large surfaces for defects and for monitoring those defects over time.

It should be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A process for detecting defects in a surface, comprising the steps of:

positioning a light source relative to the surface;

generating positional information about the position of the light source relative to the surface by using positioning indicia located on the surface;

directing a plurality of beams of light from the light source onto a region of the surface;

detecting a portion of the light which is reflected from the surface at an angle other than the angle of expected reflectance;

generating reflectance information corresponding to the light detected during said detecting step; and analyzing the reflectance information and the positional information to discern and identify the location of defects in the surface.

2. The process of claim 1, further comprising maintaining a record of surface defects discerned during said analyzing step.

3. The process of claim 1, further comprising the steps of repositioning the light source relative to the surface such that the beams of light may be directed onto a different region of the surface and repeating the preceding steps whereby defects in multiple regions of the surface may be detected.

4. The process of claim 3, wherein said repositioning step further comprises:

sensing a portion of light which passes through an aperture in the surface, said sensing being performed by a light sensor;

generating aperture-positional signals corresponding to the light sensed during said sensing step; and analyzing the aperture-positional signals to determine the present position of the light sensor relative to the aperture.

5. The process of claim 4, wherein said sensing step comprises introducing a portion of light which passes through the aperture in the surface into a line scan gauge.

6. The process of claim 1, wherein said directing step comprises directing a plurality of beams of light at non-normal angles of expected incidence onto a region of the surface.

7. The process of claim 6, wherein said directing step includes directing beams of light which are arranged in at least two groups, with each group positioned in a substantially non-parallel relationship with at least one other such group.

8. The process of claim 6, wherein said detecting step comprises introducing a portion of the reflected light into a video camera.

9. The process of claim 6, wherein said analyzing step comprises processing the reflectance information by computer.

10. The process of claim 6, wherein said step of generating reflectance information comprises introducing signals into an output device producing a human-readable form of output.

11. A process for detecting defects in a surface, comprising the steps of:

positioning a light source relative to the surface; directing semi-collimated light generated by the light source at non-normal angles of expected incidence onto a region of the surface;

generating positional information about the position of the light source relative to the surface by using positioning indicia located on the surface;

detecting a portion of the light which is reflected from the surface at an angle other than the angle of expected reflectance;

generating signals which correspond to the light detected during said detecting step;

filtering the signals generated during said generating step through a noise filter to produce arithmetic filter outputs;

analyzing the arithmetic filter outputs to discern defects in the surface; and analyzing the positional information to identify the location of defects in the surface.

12. A system for detecting defects in a surface, comprising:

a light source capable of directing a plurality of beams of light onto a region of the surface;

a positioning indicia locator in communication with said light source, said positioning indicia locator capable of determining the position of said light source relative to positioning indicia located on the surface;

a light detector capable of detecting light reflected from the surface and of generating signals corresponding to the presence of such reflected light;

a reflectance signal convertor in communication with said light detector, said convertor capable of converting the signals generated by said light detector into analyzable reflectance signals; and an analyzer in communication with said reflectance signal convertor, said analyzer capable of analyzing the analyzable reflectance signals to discern defects in the surface.

13. The system of claim 12, further comprising a positioning apparatus capable of altering the position of the surface relative to said light source such that defects in multiple regions of the surface may be detected.

14. The system of claim 12, wherein said positioning indicia locator comprises:

a light sensor capable of sensing a portion of light which passes through an aperture in the surface, and of generating signals corresponding to the presence of such sensed light;

a surface position analyzer in communication with said light sensor capable of analyzing the aperture-positional signals to determine the present position of said light sensor relative to the aperture.

15. The system of claim 14, wherein said light sensor comprises a line scan gauge.

16. The system of claim 12, further comprising a record-keeping apparatus in communication with said analyzer, said record-keeping apparatus capable of maintaining a record of surface defects discerned by said analyzer.

17. The system of claim 12, wherein said light source is further configured to direct a plurality of beams of light at non-normal angles of expected incidence onto a region of the surface.

18. The system of claim 12, wherein said light source comprises more than one light source positioned to generate beams of light, said light sources positioned such that the beams of light are arranged in at least two groups, with each group positioned in a substantially non-parallel relationship with at least one other such group.

19. The system of claim 12, wherein said light detector comprises a video camera.

20. The system of claim 12, wherein said analyzer comprises a computer.

21. The system of claim 12, wherein said reflectance signal convertor comprises an output device producing a human-readable form of output.

22. The system of claim 12, further comprising a mounting fixture for use in inspecting regions on the surface of a substantially cylindrical member, said mounting fixture including a chord beam configured to slidably engage an edge of the cylindrical member.

23. The system of claim 22, wherein said mounting fixture further comprises compensation means permitting full rotation of said fixture when said fixture is engaged with the edge of a cylindrical member which is not perfectly circular.

24. A system for detecting defects in a surface, comprising:

a light capable of directing semi-collimated light at non-normal angles of expected incidence onto a region of the surface;

a positioning indicia locator in communication with said light source, said positioning indicia locator capable of determining the position of said light source relative to positioning indicia located on the surface;

a light detector capable of detecting a portion of the light which is reflected from the surface at an angle other than the angle of expected reflectance and of generating signals which correspond to such detected light;

a noise filter capable of filtering the signals generated by said light detector to produce arithmetic filter outputs; and an analyzer capable of analyzing the arithmetic filter outputs to discern defects in the surface.

25. The system of claim 24, wherein said light source comprises at least one fiber optic light panel.

26. The system of claim 24, wherein said analyzer comprises a defect locator capable of determining the location of a detected defect relative to a predetermined point on the surface.

27. The system of claim 24, wherein said analyzer comprises an estimator capable of determining the location and extent of a detected surface defect.

28. The system of claim 24, wherein said convertor comprises an output device producing a human-readable form of output.

* * * * *